United States Patent [19]

Watase et al.

[11] Patent Number: 4,502,323
[45] Date of Patent: Mar. 5, 1985

[54] METHOD AND APPARATUS FOR PERFORMING A HYDRAULIC PRESSURE TEST ON A TUBE

[75] Inventors: Tosio Watase; Koichi Mori; Kazuo Sasaki; Katsumi Onizuka; Yuzo Yoshikawa; Takeshi Fujita, all of Osaka, Japan

[73] Assignee: KK Yamamoto Suiatsu Kogyosho, Osaka, Japan

[21] Appl. No.: 509,514

[22] Filed: Jun. 30, 1983

[30] Foreign Application Priority Data

Jun. 30, 1982 [JP] Japan ................................. 57-114392

[51] Int. Cl.³ .............................................. G01M 3/28
[52] U.S. Cl. .................................................. 73/49.6
[58] Field of Search ....................... 73/49.5, 49.6, 49.1

[56] References Cited

U.S. PATENT DOCUMENTS 4,362,049 12/1982 Horton .............................. 73/49.1 X

FOREIGN PATENT DOCUMENTS 7609244 2/1978 Netherlands ........................ 73/49.1
746230 7/1980 U.S.S.R. ............................. 73/49.5

Primary Examiner—Gerald Goldberg
Assistant Examiner—Joseph W. Roskos
Attorney, Agent, or Firm—Sughrue, Mion, Zinn, Macpeak & Seas

[57] ABSTRACT

A method of performing hydraulic pressure test of tubes includes the step of performing hydraulic pressure test of the tube. The ends of a test tube are sealed by using closing caps at the respective opposite ends of the test tube which has been filled with water under a completely air-purged condition. The closing caps are held in place during conveyance of the test tube with the opposite ends thereof sealed by the closing caps, to a position at which the test tube is subject to the steps of a hydraulic pressure test including sealing to prevent the filled water from leaking; introducing high pressure water in the hydraulic pressure test step with the closing caps attached to the test tube; maintaining the inner high pressure of the test tube due to the high pressure water; reducing the inner pressure of the test tube through the closing caps, upon the completion of the hydraulic test; and removing the closing caps from the test tube.

6 Claims, 7 Drawing Figures

METHOD AND APPARATUS FOR PERFORMING A HYDRAULIC PRESSURE TEST ON A TUBE

BACKGROUND OF THE INVENTION

The present invention is directed to a method and apparatus for performing a hydraulic pressure test on a tube and more specifically to a method and apparatus for sequentially moving a tube to be tested through a plurality of positions while capping the ends of the tube underwater and subsequently increasing the pressure of the water within the tube after the tube has been raised above the water level.

In the conventional hydraulic pressure testing of tubes, the tube to be tested, hereinafter referred to as the test tube, is filled with low pressure water in one position with the subsequent introduction of high pressure water into the test tube in the same position. Thus, the time required for the testing of a single test tube is the sum of time required for filling the test tube with water, the time required for the high pressure water application and the time required for handling the test tube to and from the test position. Thus, the conventional prior method and the apparatus involved a considerable expenditure of time.

SUMMARY OF THE INVENTION

The present invention provides a new and improved method and apparatus for performing the hydraulic pressure test on a tube wherein the step of filling a tube with water is performed separately from the step of applying high pressure to the filled test tube. By previously filling the test tube with water under completely air-purged conditions, closing the ends of the test tube with closing caps and conveying the filled test tubes to a hydraulic pressure test position, the time required for the step of hydraulic pressure testing will only be the sum of the time required for the application of high pressure water and the time required for conveying the test tube. Thus, the method and apparatus according to the present invention results in a remarkable improvement in operational efficiency as compared with foregoing conventional method.

The present invention provides a new and improved method and apparatus for performing the hydraulic pressure test on a tube wherein the test tube enclosing caps are provided with dual check valves for controlling the application of hydraulic pressure to a peripheral seal and for automatically closing the outlet in each end cap upon stopping the application of high pressure water to the test tube.

The present invention provides a new and improved method for performing the hydraulic pressure test on a tube comprising the steps of transferring the hollow, elongated tube from a first conveying means to a first support means located in a water tank, lowering the first support means into the water within the tank and automatically transferring the tube to a second support means located in the tank below the water level, applying and sealing end caps to opposite ends of said tube while said tube is underwater, raising said second support means to a test position, applying high pressure hydraulic fluid to the interior of said tube through at least one end cap, removing said end caps and transferring said tube to a second conveying means.

The present invention provides a new and improved apparatus for performing the hydraulic pressure test on a tube comprising a water tank, a first conveying means for conveying a tube to said tank, first and second adjustable tube supporting means located within said tank, first transfer means associated with said first conveying means for transferring a tube from said first conveying means to said first support means, second transfer means associated with said first support means for automatically transferring said tube means to said second support means as said first support means is lowered within said tank, end cap support means adapted to position end caps in alignment with opposite ends of said tube, end cap applying means adapted to locate said end caps in opposite ends of said tube in sealed relation thereto, hydraulic pressure application means adapted to be engaged with opposite ends of said tube when said second support means is raised to position tube above the water and including means for removing said end cap subsequent to the hydraulic pressure test, second conveying means and third transfer means for transferring said tube from said second support means to said second conveying means.

The foregoing and other objects, features and advantages of the invention will be apparent from the following more particular description of a preferred embodiment of the invention as illustrated in the accompanying drawings.

DETAILED DESCRIPTION OF THE INVENTION

Figure 1:
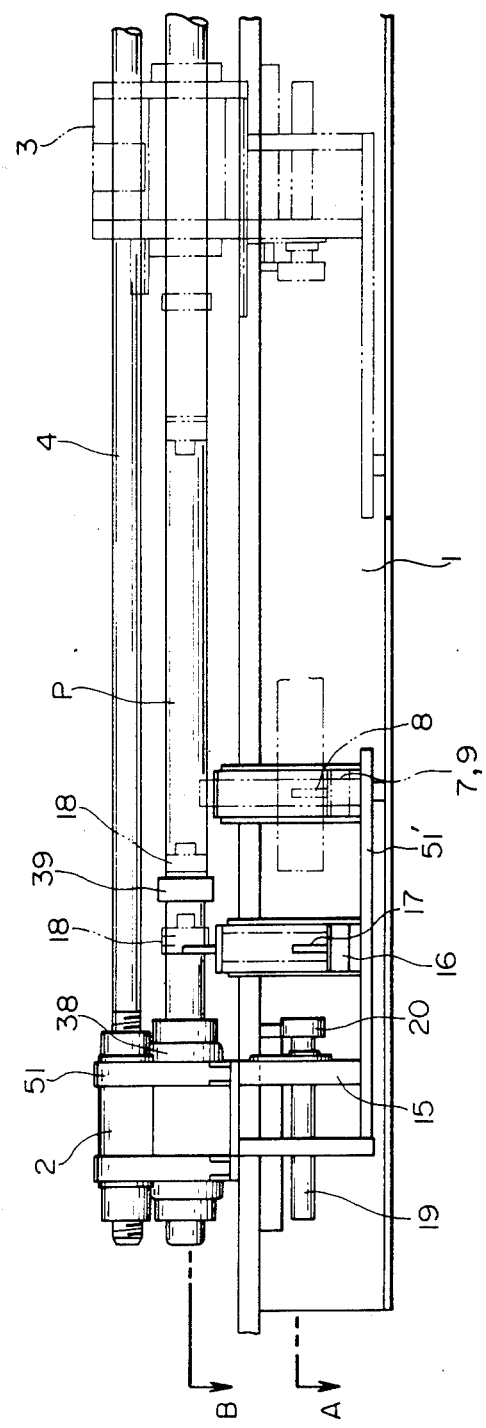
FIG. 1 is a side elevation view, partly in section and partly in phantom lines showing the apparatus according to the present invention.
Figure 5:
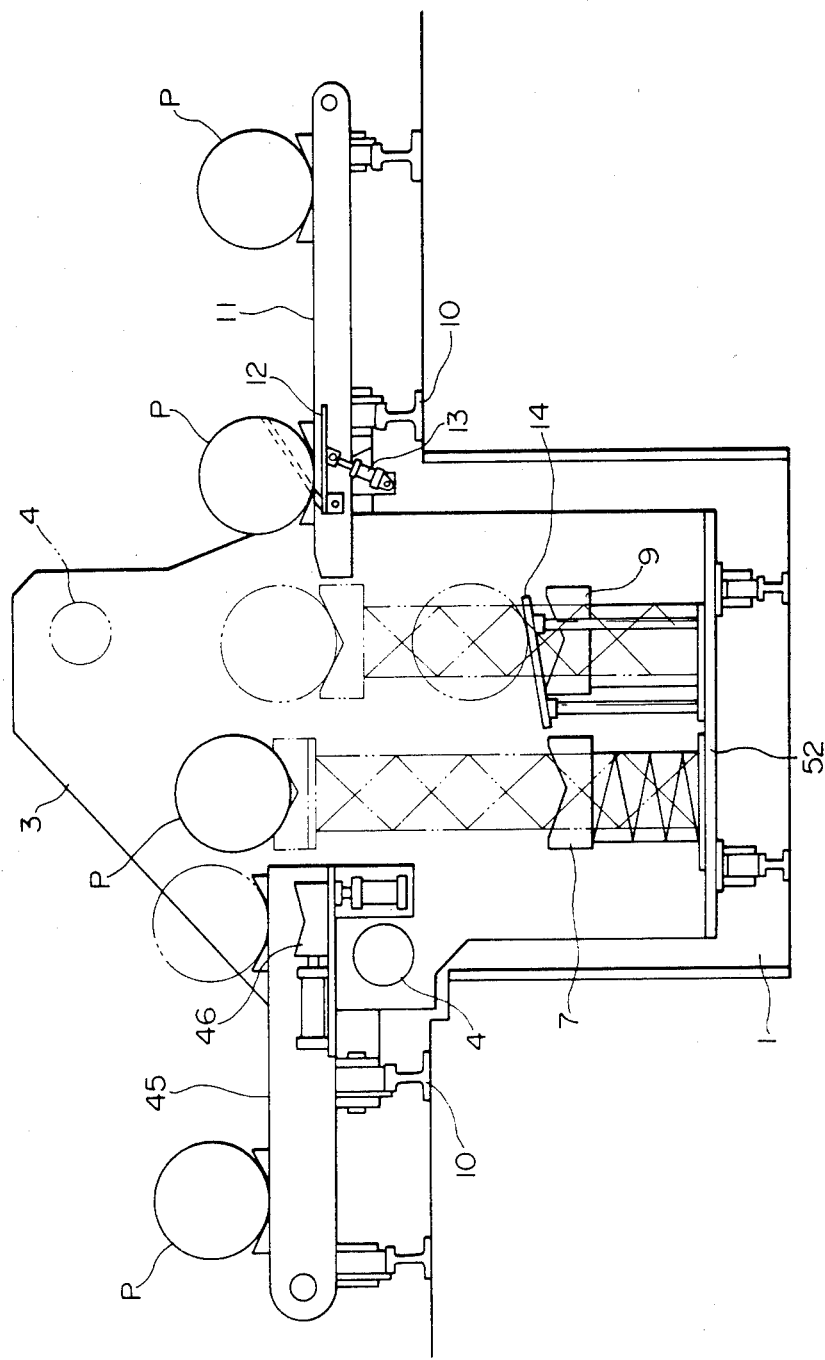
FIG. 5 is a sectional view showing an end view of the apparatus in FIG. 4.

The apparatus according to the present invention as shown in FIG. 1 is comprised of a water tank 1 adapted to be filled with water for the purpose of filling a test tube P with water for a hydraulic pressure test. The head stock 2 and a tail stock 3 constitute means for applying pressure to opposite ends of the test tube P. Head stock 2 and tail stock 3 are adjustably connected to each other by a tension rod 4. The head stock 2 is fixed to the base of the tank 1 while the tail stock 3 is supported on a truck which is movably supported by a plurality of rails 10 as best seen in FIG. 5 so as to accomodate test tubes P of varying length. The tension rod 4 is provided with one or more lock grooves 5 for fixing the tail stock 3 at desired locations spaced from the tail stock 2 in order to accomodate the length of any test tube P. The tail stock 3 can be fixed relative to the tension rod 4 by means of a locking device 6 provided on the tail stock frame 52 which is engageable in the groove 5 for the purpose of bearing the thrust load generated during the hydraulic pressure test.

The tube P to be tested is supplied by means of an input conveyor 11 in a position parallel to the length of the water tank 1 adjacent the upper edge thereof. A lever 12 is pivotably supported on the conveyor frame 11 beneath the pipe P and upon being pivoted upwardly from the solid line position to the dotted line position shown in FIG. 5 by means of a hydraulic piston and cylinder device 13 the pipe will be transferred onto a pair of vertically adjustable pipe receiving devices 9 which are movable between a solid line retractive position and a raised dotted line position as shown in FIG. 5 by means of suitable hydraulic cylinders 8. A second pair of pipe lifting devices 7 are disposed immediately adjacent the pair of pipe receiving devices 9. The pipe lifting devices 7 are also actuatable by suitable hydraulic devices 8 between a lower solid line position and a raised dotted line position as shown in FIG. 5. Once the test pipe P has been transferred to the receiving devices 9, the receiving devices may be lowered to immerse the pipe within a water filled tank 1. As the receiving devices 9 move below the level of the slanted skid member 14, the pipe will automatically be transferred onto the lowered lifting devices 7, thereby placing the test pipe P in position for capping the ends thereof.

Figure 6A:
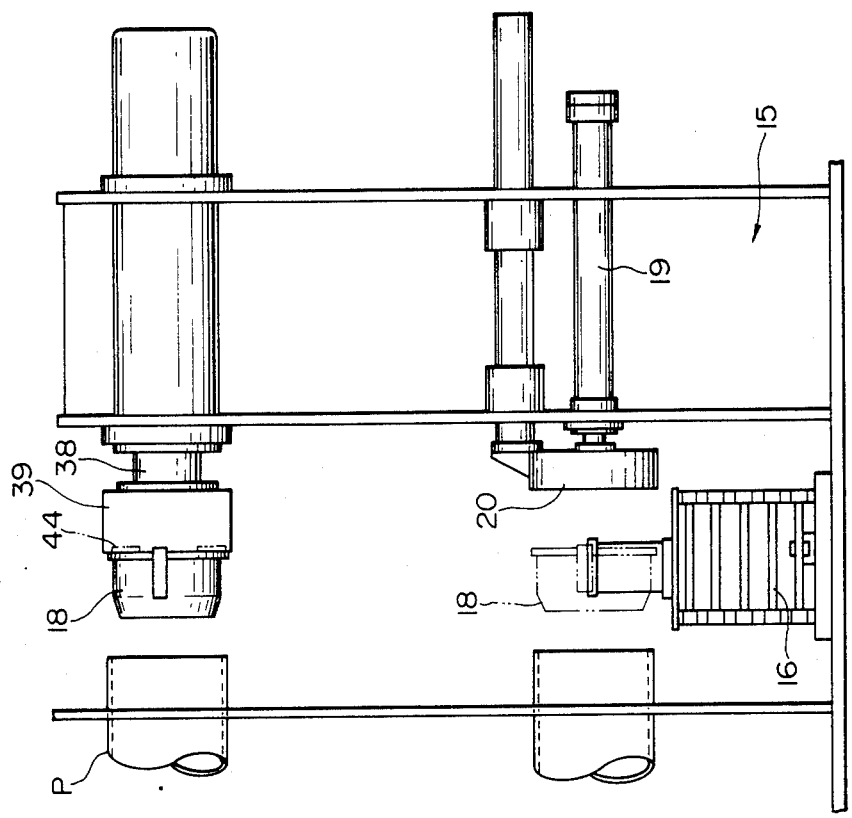
FIG. 6A is an enlarged detailed view of the end piece support stand shown in FIG. 1.
Figure 6B:
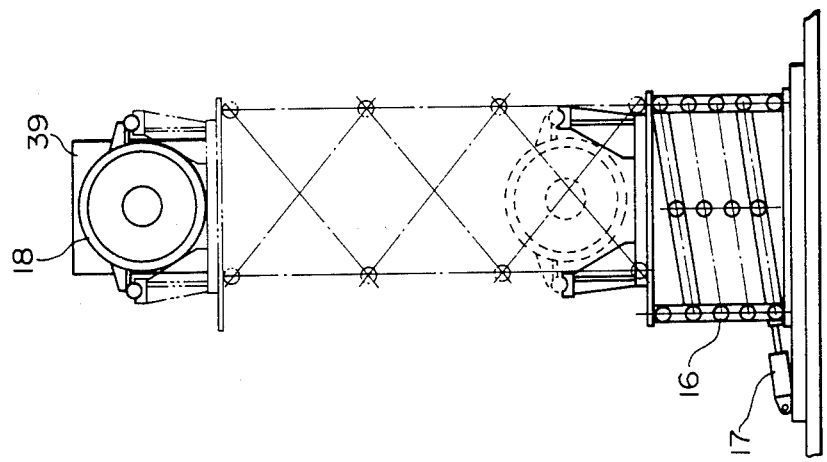
FIG. 6B is a side elevation view of the support stand in FIG. 6A in the extended position.

A pair of closing caps 18 which have been removed from the previously tested pipe in a manner to be described hereinafter, are supported by a pair of lifting devices 16 for movement between a raised position and a lowered position as shown in FIGS. 6A and 6B by means of hydraulic devices 17 operatively connected thereto. When the end caps are brought to their lowest position, they are disposed in alignment between the ends of the pipe and a pair of automatic closing cap mounting devices 15 mounted on the frames 51' and 52' of the head stock 2 and the tail stock 3.

Figure 2:
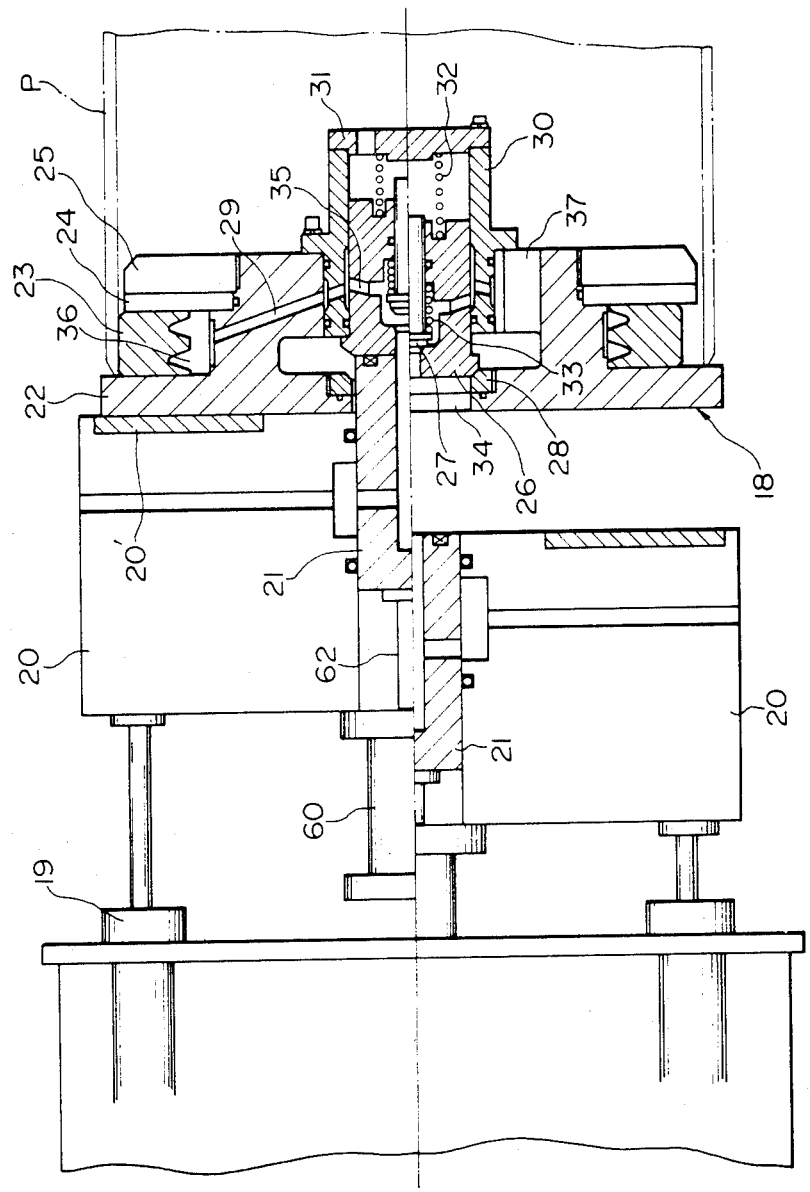
FIG. 2 is a partial sectional view taken along the line indicated by the arrow A in FIG. 1.

The mounting machine 15 is comprised of a mounting head 20 and an oil cylinder 19 for pushing the mounting head 20 toward test tube P. The mounting head 20 stops in the position at which it is disposed in contact with the closing cap 18 which has been centered by the closing cap lifting device 16. As best shown in FIG. 2, the closing cap 18 is comprised of a body 22 which is detachably connected to the mounting head 20 by means of an electro-magnet 20' which is provided in the surface of the mounting head 20. Once the closing caps 18 have been mounted on respective mounting heads, the oil cylinders 19 are actuated to insert the closing caps 18 into the opposite ends of the test tube P. Initially the end cap 18 is located within the end of the test tube P in an unsealed condition as illustrated in the lower half of FIG. 2. In addition to the closing cap body 22, the closing cap includes a resilient sealing ring 23 which is located in the groove defined between the cap body 22 and a keeper plate 24 secured on the cap body 22 by means of a guide ring 25 threaded on the cap body 22. The cap body 22 is provided with a central aperture having a tubular valve guide 30 secured therein in which a check valve 26 is mounted for reciprocating movement. The check valve 26 is adapted to mate with a valve seat 28 secured to the cap body 22 and is normally biased into closing engagement with the valve seat 28 by means of the spring 32 which is seated against a keeper member 31 connected to the end of the valve guide 30. The check valve 26 is provided with a central bore having a presealing check valve 27 slidably disposed therein. The check valve 27 is normally biased into the closed position by means of a spring 33. A passage or central bore 34 of the check valve 26 is connected to an operating chamber circumferentially inward of the resilient sealing ring 23 by means of a passage 29 provided in the cap body 22 and a radial passage 35 in the check valve 26 and valve guide 30. A passage 37 is provided in the cap body 22 radially outwardly of the valve guide 30 which communicates with the central bore 34 in the cap body 22 when the check valve 26 moves away from the valve seat 28.

The mounting head 20 is provided with a water conveying head 21 which is slidably mounted in a central bore in the mounting head 20. The water conveying head 21 is adapted to be reciprocated by means of a piston 62 extending from a double acting hydraulic cylinder 60. Once the sealing caps 18 have been located within the ends of the test tube P, the water conveying head 21 is shifted to the position shown in the upper half of FIG. 2 wherein the check valve 26 is moved away from the valve seat 28. Upon introducing water under pressure of 10 kg/cm$^2$–30 kg/cm$^2$ through the various passages in the mounting head 20 and the water conveying head 21, the check valve 27 will be opened against the force of the spring 33 by the water pressure. Thus, water under pressure will be applied to the sealing ring 23 through the passages 35 and 29. When the pressure in the sealed packing chamber 36 reaches 5 kg/cm$^2$–10 kg/cm$^2$ the sealing ring 23 will be caused to move radially outwardly into engagement with the inner wall of the test tube P, thus securing the cap bodies 18 in the opposite ends of the test tube P. Thus, upon retraction of the water conveying head 21 and de-energization of the electro-magnet 20' and the retraction of the head 20, the check valves 26 and 27 will be closed to completely seal the water within the test tube P.

The test tube P which is now filled with water and sealed at both ends is lifted by the main lifting devices 7 to the hydraulic pressure test position above the surface of the water within the tank 1. The test tube P is shown in the test position in solid lines in FIGS. 1 and 4, and is disposed in alignment with the oil cylinders 38 mounted in the head stock 2 and the tail stock 3, respectively. A high pressure water conveying head 39 is secured to the end of each oil cylinder 38 for introducing high pressure water into the test tube P through the closing cap 18. Upon actuation of the oil cylinders 38 the test tube P will be engaged under pressure at opposite ends by the water conveying heads 39, one of which is shown in detail in FIG. 3. High pressure water is introduced through the high pressure water conveying head 39 through the passage 40. A sealing ring 41 seals the contact surface between the water conveying head 39 and the closing cap 18 to prevent the high pressure water from leaking outside. The high pressure water conveying head 39 is held securely against the closing cap 18 by means of electro-magnet 44 which engages the cap body 22 of the closing cap 18. Upon the introduction of high pressure water, the main check valve 26 provided in the closing cap 18 will be opened, thereby allowing high pressure water to flow into the test tube P through the passages 34 and 37 in the sealing head 2. The thus increased pressure in the test tube P opens the check valve 27 to simultaneously admit the passage of high pressure water to the sealing ring chamber 36 so as to increase the pressure on the sealing ring 23 to compensate for the increased pressure within the test tube P. When the water pressure within the tube reaches a pre-determined value, the introduction of high pressure water is stopped and the integrity of the tube is checked. The main check valve 26 and the check valve 27 are automatically closed by the springs 32 and 33 due to the equalization of pressure.

Figure 3:
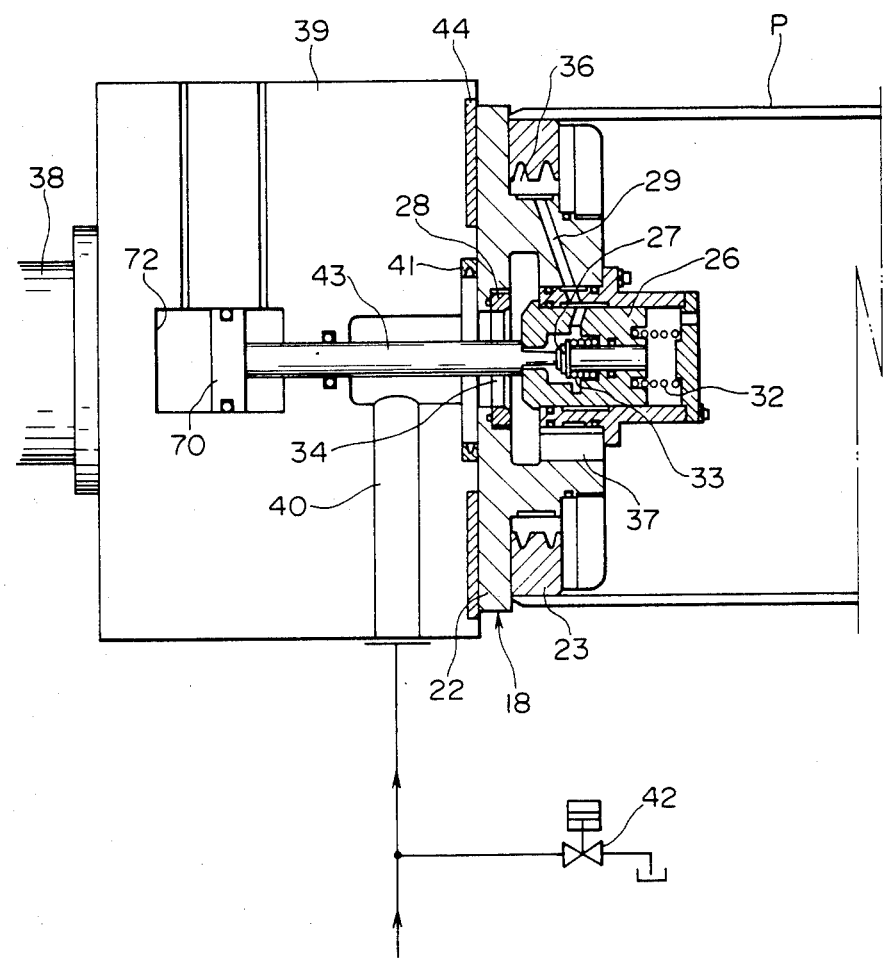
FIG. 3 is a cross-sectional view taken along the line indicated by the arrow B in FIG. 1.
Figure 4:
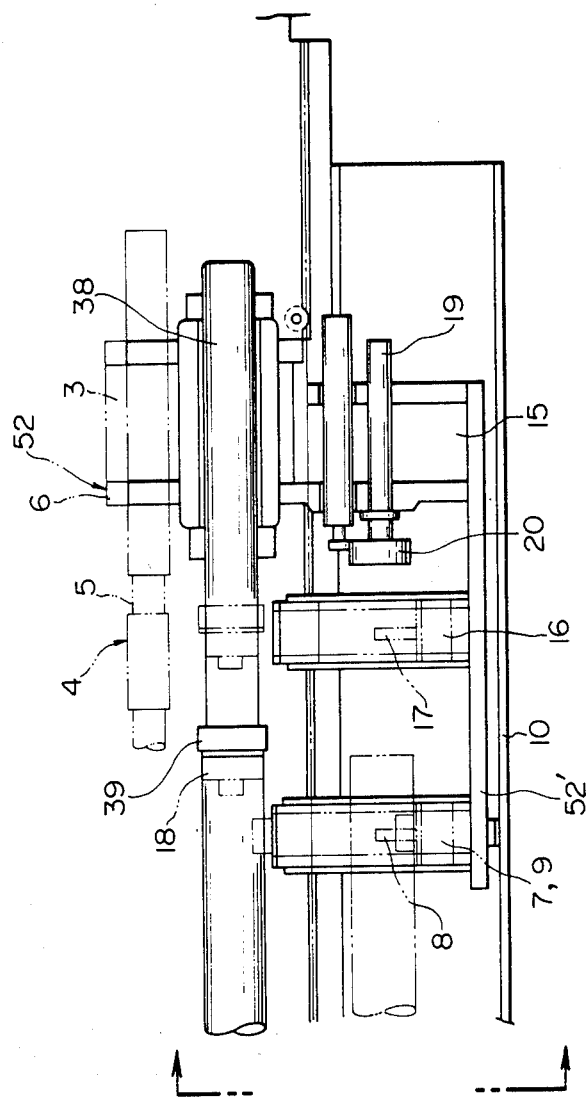
FIG. 4 is a detailed side elevation view, partly in section and partly in phantom line, of the right hand side of the apparatus shown in FIG. 1.

Upon completion of the water pressure test, a pressure reducing valve 42, connected to the high pressure water conveying head 39 is opened to immediately decrease the pressure within the passage 40. At the same time a valve push rod 43 located within the high pressure conveying head 39 is actuated by means of a hydraulically operated piston 70 located in a double acting hydraulic cylinder 72 to open the main check valve 26 and the check valve 27 in the respective closing cap as shown in FIG. 3 and to thereby discharge the water from the test tube P and from the sealing ring pressure chamber 36. Thus, the inner pressure in the test tube P returns to an atmospheric pressure and the pressure in the sealing ring pressure chamber 36 is also decreased to atmospheric pressure. Thus, the sealing ring 23 will return to its original dimensions due to its own elasticity.

Upon completion of the above-mentioned pressure reducing step, each of the respective closing caps 18 held at the opposite ends of the test tube P are effectively released from the test tube, and since they are attracted to the heads 39 by means of the electro-magnets 44, the operation of the oil cylinders 38 to retract the heads 39 away from the ends of the test tube P will cause the removal of the end closing caps 18 from the opposite ends of the test tube P. Thus, the closing caps 18 will be disposed in the position shown in FIG. 6A. Upon energization of the lifting device 16 from the lower position shown in FIG. 6 to upper position, the closing caps 18 will be supported by the lifting devices 16. The magnets 44 can be de-energized to terminate the delivery. The lifting devices 16 can then be brought down to the lowermost position for closing the next test tube P.

Upon completion of the hydraulic pressure test, the test tube P is received by a V-shaped receiving stand 46 and placed on a discharge conveyor 45 to be removed, thus completing one hydraulic test cycle.

While the invention has been particularly shown and described with reference with a preferred embodiment thereof, it will be understood by those in the art that various changes in form and details may be made therein without departing from the spirit and scope of the invention.

What is claimed is:

1. An apparatus for performing a hydraulic pressure test on a tube comprising a water tank, tube support means located in said water tank for lowering and raising a tube into and out of the water tank, a pair of valved end caps adapted to be inserted into opposite ends of said tube, end cap support means adapted to position said caps in alignment with opposite ends of said tube when said tubes are lowered into said water tank, end cap applying means adapted to insert said end cap into opposite ends of said tube in sealed relation thereto, hydraulic pressure application means adapted to be engaged with opposite ends of said valved end caps when said tube support means is raised to a position above the water tank for introducing water under high pressure through said valved end caps, and means associated with said hydraulic pressure means for removing said end caps subsequent to the hydraulic pressure test, wherein said tube support means is comprised of a first supporting device adapted to receive a tube above said water tank and lower said tube into said water tank, a second supporting device being moveably mounted in said tank for supporting a tube in a lowered position within the tank for the application of end caps thereto and a second position above said water tank for carrying out the hydraulic pressure test and cam means associated with said first supporting device for automatically transferring a tube from said first supporting device to said second supporting device as said first supporting device lowers the tube into said water tank.

2. An apparatus for performing a hydraulic pressure test on a tube comprising a water tank, tube support means located in said water tank for lowering and raising a tube into and out of the water tank, a pair of valved end caps adapted to be inserted into opposite ends of said tube, end cap support means adapted to position said caps in alignment with opposite ends of said tube when said tubes are lowered into said water tank, end cap applying means adapted to insert said end cap into opposite ends of said tube in sealed relation thereto, hydraulic pressure application means adapted to be engaged with opposite ends of said valved end caps when said tube support means is raised to a position above the water tank for introducing water under high pressure through said valved end caps, and means associated with said hydraulic pressure means for removing said end caps subsequent to the hydraulic pressure test, wherein said each of said end caps is comprised of a sealing head adapted to be inserted into an end of said test tube, said sealing head having an annular resilient packing seal located in an annular chamber about the outer circumference of said sealing head, passage means in said sealing head for introducing water under pressure into said chamber for expanding said packing seal into engagement with the interior surface of said tube, passage means in said sealing head for introducing water into the interior of said tube, main check valve means located in said sealing head for controlling the flow of water under pressure into said sealing head and auxillary valve means associated with said main check valve means for controlling the flow of water to said chamber.

3. An apparatus as set forth in claim 2 wherein said means for inserting said end caps into opposite ends of said pipe are each comprised of a mounting head, power means for moving said mounting head toward and away from the end of said pipe, a movable water conveying head carried by said mounting head for engagement with said main check valve means, second power means for moving said water conveying head into and out of engagement with said main check valve means for opening and closing said main check valve means and water passage means in said mounting head and said water conveying head for supplying water under pressure to said main check valve means for opening said auxilliary valve means to pressure said chamber.

4. An apparatus as set forth in claim 3 further comprising magnetic means associated with said mounting head for engaging and holding said end cap means on said mounting head during insertion into the respective end of a pipe to be tested.

5. An apparatus as set forth in claim 2 wherein each of said hydraulic pressure application means is comprised of a valve push rod slidably mounted therein, piston and cylinder means for reciprocating said push rod into and out of engagement with said main check valve means and said auxilliary valve means, water passage means extending through said hydraulic pressure application means for supplying water under high pressure into said chamber and the interior of said tube upon opening of said main check valve means and said auxilliary valve means and means for reciprocating said hydraulic pressure application means into and out of engagement with said end cap.

6. An apparatus as set forth in claim 5 further comprising magnetic means carried by said hydraulic pressure application means for supporting said end cap on said hydraulic pressure application means for withdrawing said end cap upon movement of said hydraulic application means away from said tube upon completion of testing.

* * * * *